(12) United States Patent
Chen et al.

(10) Patent No.: US 9,492,399 B2
(45) Date of Patent: Nov. 15, 2016

(54) METHOD OF TREATING IRON DEFICIENCY

(71) Applicant: Industrial Technology Research Institute, Chutung, Hsin Chu (TW)

(72) Inventors: Chih-Lung Chen, Taichung (TW); Wen-Yuan Hsieh, Zhubei (TW); Chen-Hsuan Lin, Pingtung (TW); Su-Yo Lin, Hsinchu (TW); Shin-Yi Huang, Hsinchu (TW); Yuan-Hung Hsu, Hsinchu (TW); Shian-Jy Wang, Zhudong Township (TW); Hsin Jung Huang, New Taipei (TW)

(73) Assignee: MegaPro Biomedical Co., Ltd., Taipei (TW)

(*) Notice: Subject to any disclaimer, the term of this patent is extended or adjusted under 35 U.S.C. 154(b) by 0 days.

(21) Appl. No.: 14/796,332

(22) Filed: Jul. 10, 2015

(65) Prior Publication Data

US 2016/0008292 A1 Jan. 14, 2016

Related U.S. Application Data

(60) Provisional application No. 62/023,533, filed on Jul. 11, 2014.

(51) Int. Cl.
 *A61K 9/51* (2006.01)
 *A61K 33/26* (2006.01)
(52) U.S. Cl.
 CPC ............ *A61K 9/5146* (2013.01); *A61K 33/26* (2013.01); *Y10S 514/814* (2013.01); *Y10S 977/773* (2013.01)
(58) Field of Classification Search
 None
 See application file for complete search history.

(56) References Cited

U.S. PATENT DOCUMENTS

| | | | |
|---|---|---|---|
| 5,248,492 A | 9/1993 | Groman et al. | |
| 5,554,386 A | 9/1996 | Groman et al. | |
| 7,553,479 B2 | 6/2009 | Groman et al. | |
| 7,754,702 B2 | 7/2010 | Helenek et al. | |
| 7,820,184 B2 | 10/2010 | Stritzker et al. | |
| 7,871,597 B2 | 1/2011 | Groman et al. | |
| 8,431,549 B2 | 4/2013 | Helenek et al. | |
| 2003/0032995 A1* | 2/2003 | Handy | A61N 1/406 607/103 |
| 2003/0190355 A1 | 10/2003 | Hermelin et al. | |
| 2006/0216239 A1 | 9/2006 | Zhang et al. | |
| 2007/0148095 A1 | 6/2007 | Chen et al. | |
| 2008/0081891 A1 | 4/2008 | Wang et al. | |
| 2009/0280063 A1 | 11/2009 | Kulkarni et al. | |
| 2009/0317327 A1 | 12/2009 | Pilgrimm | |
| 2011/0064675 A1 | 3/2011 | Hadjipanayis et al. | |
| 2011/0171715 A1* | 7/2011 | Chang | A61K 49/0093 435/188 |
| 2011/0182805 A1 | 7/2011 | DeSimone et al. | |
| 2011/0286938 A1 | 11/2011 | Thurman et al. | |
| 2012/0003160 A1 | 1/2012 | Wolf et al. | |
| 2012/0121649 A1 | 5/2012 | Santamaria | |
| 2012/0201760 A1 | 8/2012 | Tromsdorf et al. | |
| 2012/0203050 A1 | 8/2012 | Levy et al. | |
| 2012/0329129 A1 | 12/2012 | Chang et al. | |
| 2013/0230463 A1 | 9/2013 | Hay et al. | |
| 2013/0256583 A1 | 10/2013 | Schlenoff et al. | |
| 2013/0336897 A1 | 12/2013 | Wolf et al. | |

FOREIGN PATENT DOCUMENTS

| | | | |
|---|---|---|---|
| CN | 102349930 A | 2/2012 | |
| CN | 103303981 A | 9/2013 | |
| CN | 103341165 A | 10/2013 | |
| CN | 103405790 A | 11/2013 | |
| CN | 103469290 A | 12/2013 | |
| CN | 103601900 A | 2/2014 | |
| EP | 2481710 A1 | 8/2012 | |
| TW | I361082 B | 4/2012 | |
| WO | WO-2008/034675 A1 | 3/2008 | |
| WO | WO-2010/034319 A1 | 4/2010 | |
| WO | WO 2010034319 A1 * | 4/2010 | .......... A61K 9/5123 |
| WO | WO-2010/076237 A2 | 7/2010 | |
| WO | WO-2012/036978 A1 | 3/2012 | |
| WO | WO-2012/092305 A2 | 7/2012 | |
| WO | WO-2013/150118 A1 | 10/2013 | |
| WO | WO-2013/185032 A1 | 12/2013 | |
| WO | WO-2014/183347 A1 | 11/2014 | |

OTHER PUBLICATIONS

Mayo Clinic Staff. "Disease and Conditions Iron Deficiency Anemia." http://www.mayoclinic.org/diseasesconditions/irondeficiencyanemia/basics/symptoms/con20019327?p=1, accessed Nov. 23, 2015, 8 printed pages.*

Laurent et al "Magnetic Iron Oxide Nanoparticles: Synthesis, Stabilization, Vectorization, Physicochemical Characterizations, and Biological Applications" Chem Rev vol. 108, pp. 2064-2110. 2008.

Jahn et al "A Comparative Study of the Physicochemical Properties of Iron Isomaltoside 1000 (Monofer), a New Intravenous Iron Preparation and its Clinical Implications" European Journal of Pharmaceutics and Biopharmaceutics vol. 78, pp. 480-491. 2011.

(Continued)

*Primary Examiner* — Isaac Shomer
(74) *Attorney, Agent, or Firm* — Cesari and McKenna LLP

(57) ABSTRACT

A method of treating a condition related to iron deficiency. The method includes steps of identifying a patient having a condition related to iron deficiency and administering an effective amount of biocompatible iron oxide nanoparticles to the patient. The biocompatible iron oxide nanoparticles each contains an iron oxide core that is covered by one or more biocompatible polymers, each of which has a polyethylene glycol group, a silane group, and a linker linking, via a covalent bond, the polyethylene glycol group and the silane group.

18 Claims, No Drawings

(56) References Cited

OTHER PUBLICATIONS

Weissleder et al "Superparamagnetic Iron Oxide: Pharmacokinetics and Toxicity" American Journal of Roentgenology vol. 152, pp. 167-173. 1989.

Danielson "Structure, Chemistry, and Pharmacokinetics of Intravenous Iron Agents" Journal of the American Society of Nephrology vol. 15, pp. S93-S98. 2004.

Spinowitz et al "Ferumoxytol for Treating Iron Deficiency Anemia in CKD" Journal of the American Society of Nephrology vol. 19, pp. 1599-1605. 2008.

Balakrishnan et al "Physicochemical Properties of Ferumoxytol, a New Intravenous Iron Preparation" European Journal of Clinical Investigation vol. 39, pp. 489-496. 2009.

Ghada et al "Effect on Different Types of Oral Iron Therapy Used for the Treatment of Iron Deficiency Anemia and Their Effects on Some Hormones and Minerals in Anemic Rats" Journal of American Science vol. 6, pp. 109-118. 2010.

Weinstein et al "Superparamagnetic Iron Oxide Nanoparticles: Diagnostic Magnetic Resonance Imaging and Potential Therapeutic Applications in Neurooncology and Central Nervous System Inflammatory Pathologies, A Review" Journal of Cerebral Blood Flow and Metabolism vol. 30, pp. 15-35. 2010.

Schwenk "Ferumoxytol: A New Intravenous Iron Preparation for the Treatment of Iron Deficiency Anemia in Patients with Chronic Kidney Disease" Pharmacotherapy vol. 30, pp. 70-79. 2010.

Lu et al "FDA Report: Ferumoxytol for Intravenous Iron Therapy in Adult Patients with Chronic Kidney Disease" American Journal of Hematology vol. 85, pp. 315-319. 2010.

Tassa et al "Dextran-Coated Iron Oxide Nanoparticles: A Versatile Platform for Targeted Molecular Imaging, Molecular Diagnostics, and Therapy" Accounts of Chemical Research vol. 44, pp. 842-852. 2011.

Shen et al "Iron Oxide Nanoparticles Suppressed T Helper 1 Cell-Mediated Immunity in a Murine Model of Delayed-Type Hypersensitivity" International Journal of Nanomedicine vol. 7, pp. 2729-2737. 2012.

Heming et al "Efficacy and Toxicity of Intravenous Iron in a Mouse Model of Critical Care Anemia" Critical Care Medicine vol. 40, pp. 2141-2148. 2012.

Yessayan et al "Intravenous Iron Dextran as a Component of Anemia Management in Chronic Kidney Disease: A Report of Safety and Efficacy" International Journal of Nephrology vol. 2013, pp. 1-9. 2013.

\* cited by examiner

METHOD OF TREATING IRON DEFICIENCY

CROSS-REFERENCE TO RELATED APPLICATIONS

The present application claims the benefit of U.S. Provisional Patent Application Ser. No. 62/023,533, which was filed on Jul. 11, 2014, by Chih-Lung Chen, et al. for Method of Treating Iron Deficiency and is hereby incorporated by reference.

BACKGROUND

Parenteral iron therapy is widely used for treating conditions related to iron deficiency, including, but not limited to, anemia. Many parenteral iron formulations are commercially available, such as iron polysaccharide, iron dextran, ferric gluconate, and iron sucrose.

Current iron therapies suffer a few drawbacks. First, they have low potency and require high dosage or frequent dosing. Second, they have adverse side effects, such as anaphylaxis and hypersensitivity. Indeed, patient compliance is low due to their adverse effects.

There is a need to develop a potent and safe parenteral iron therapy.

SUMMARY

Disclosed herein is a method of treating iron-related conditions. The method includes: (i) identifying a patient having a condition related to iron deficiency, e.g., iron deficiency anemia; and (ii) administering an effective amount of biocompatible iron oxide nanoparticles to the patient.

In other words, the method uses biocompatible iron oxide nanoparticles to treat iron deficiency conditions. The method exhibits an unexpected efficacy and safety profile in treatment of an iron deficiency condition.

The biocompatible iron oxide nanoparticles each contain an iron oxide core that is covered by one or more biocompatible polymers, each of which has a polyethylene glycol group, a silane group, and a linker that links, via a covalent bond, the polyethylene glycol group and the silane group.

Generally, the biocompatible iron oxide nanoparticles each have a particle size of 3-1000 nm. In one example, they each have a particle size of 15-200 nm.

The iron oxide core in each of the biocompatible iron oxide nanoparticles typically has a size of 2-50 nm (e.g., 10-25 nm).

In each of the biocompatible polymers, which cover the iron oxide cores, the polyethylene glycol group typically has 5-1000 oxyethylene units (e.g., 10-200 oxyethylene units), and the silane group typically contains a $C_{1-10}$ alkylene group (e.g., a $C_3$-$C_{10}$ alkylene group).

The details of one or more embodiments are set forth in the description below. Other features, objects, and advantages of the embodiments will be apparent from the description and the claims.

DETAILED DESCRIPTION

In the following detailed description, for purposes of explanation, numerous specific details are set forth in order to provide a thorough understanding of the disclosed embodiments. It will be apparent, however, that certain embodiments may be practiced without these specific details.

The method of this invention treats an iron deficiency condition using biocompatible iron oxide nanoparticles, each of which contains an iron oxide core covered by one or more biocompatible polymers.

The biocompatible polymers are biodegradable and non-toxic to cells. Silane-containing biocompatible polymers, which can be easily functionalized as shown below, are suitable for preparation of biocompatible iron oxide nanoparticles required by this method.

An exemplary biocompatible polymer has the following formula:

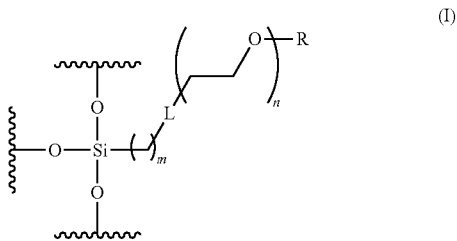

(I)

In formula (I), R is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, heteroaryl, a $C_1$-$C_{10}$ carbonyl group, or a $C_1$-$C_{10}$ amine group; L is a linker; m is 1 to 10; and n is 5 to 1000.

A linker can be O, S, Si, $C_1$-$C_6$ alkylene, a carbonyl moiety containing two carbonyl groups and 2-20 carbon atoms, or a group having one of the following formulas:

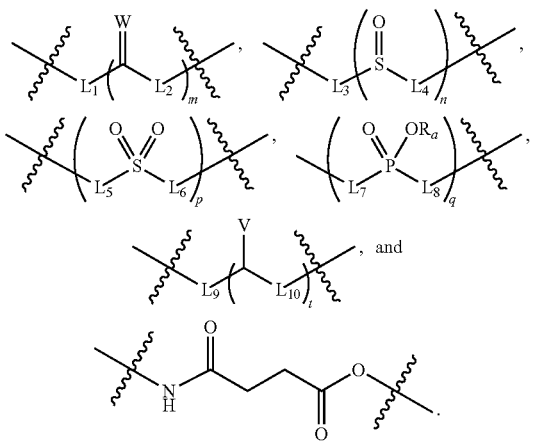

In these formula, each of m, n, p, q, and t, independently, is 1-6; W is O, S, or $NR_b$; each of $L_1$, $L_3$, $L_5$, $L_7$, and $L_9$, independently, is a bond, O, S, or $NR_c$; each of $L_2$, $L_4$, $L_6$, $L_8$, and $L_{10}$, independently, is a bond, O, S, or $NR_d$; and V is $OR_e$, $SR_f$, or $NR_gR_h$, in which each of $R_a$, $R_b$, $R_c$, $R_d$, $R_e$, $R_f$, $R_g$, and $R_h$, independently, is H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical.

Another exemplary biocompatible polymer has the following formula:

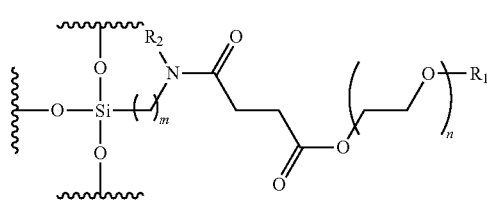

In formula (II), $R_1$ is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, heteroaryl, a $C_1$-$C_{10}$ carbonyl group, or a $C_1$-$C_{10}$ amine group; $R_2$ is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, or heteroaryl; m is 1 to 10 (e.g., 3-10); and n is 5 to 1000 (10-200). In a preferred embodiment, $R_2$ is H and the linker in formula (II) is

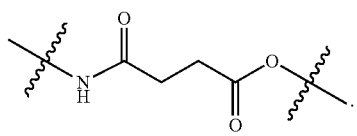 [SMILES: *NC(=O)CCC(=O)O*]

The term "aliphatic" herein refers to a saturated or unsaturated, linear or branched, acyclic, cyclic, or polycyclic hydrocarbon moiety. Examples include, but are not limited to, alkyl, alkylene, alkenyl, alkenylene, alkynyl, alkynylene, cycloalkyl, cycloalkylene, cycloalkenyl, cycloalkenylene, cycloalkynyl, and cycloalkenylene moieties. The term "alkyl" or "alkylene" refers to a saturated, linear or branched hydrocarbon moiety, such as methyl, methylene, ethyl, ethylene, propyl, propylene, butyl, butylenes, pentyl, pentylene, hexyl, hexylene, heptyl, heptylene, octyl, octylene, nonyl, nonylene, decyl, decylene, undecyl, undecylene, dodecyl, dodecylene, tridecyl, tridecylene, tetradecyl, tetradecylene, pentadecyl, pentadecylene, hexadecyl, hexadecylene, heptadecyl, heptadecylene, octadecyl, octadecylene, nonadecyl, nonadecylene, icosyl, icosylene, triacontyl, and triacotylene. The term "alkenyl" refers to a linear or branched hydrocarbon moiety that contains at least one double bond, such as —CH=CH—CH$_3$ and —CH=CH—CH$_2$—. The term "alkynyl" refers to a linear or branched hydrocarbon moiety that contains at least one triple bond, such as —C≡C—CH$_3$ and —C≡C—CH$_2$—. The term "cycloalkyl" refers to a saturated, cyclic hydrocarbon moiety, such as cyclohexyl and cyclohexylene.

The term "heteroaliphatic" herein refers to an aliphatic moiety containing at least one heteroatom (e.g., N, O, P, B, S, Si, Sb, Al, Sri, As, Se, and Ge). The term "heterocycloalkyl" refers to a cycloalkyl moiety containing at least one heteroatom. The term "oxyaliphatic" herein refers to an —O-aliphatic. Examples of oxyaliphatic include methoxy, ethoxy, n-propoxy, isopropoxy, n-butoxy, iso-butoxy, sec-butoxy, and tert-butoxy.

The term "aryl" herein refers to a $C_6$ monocyclic, $C_{10}$ bicyclic, $C_{14}$ tricyclic, $C_{20}$ tetracyclic, or $C_{24}$ pentacyclic aromatic ring system. Examples of aryl groups include, but are not limited to, phenyl, phenylene, naphthyl, naphthylene, anthracenyl, anthrcenylene, pyrenyl, and pyrenylene. The term "heteroaryl" herein refers to an aromatic 5-8 membered monocyclic, 8-12 membered bicyclic, 11-14 membered tricyclic, and 15-20 membered tetracyclic ring system having one or more heteroatoms (such as O, N, S, or Se). Examples of a heteroaryl group include, but are not limited to, furyl, furylene, fluorenyl, fluorenylene, pyrrolyl, pyrrolylene, thienyl, thienylene, oxazolyl, oxazolylene, imidazolyl, imidazolylene, benzimidazolyl, benzimidazolylene, thiazolyl, thiazolylene, pyridyl, pyridylene, pyrimidinyl, pyrimidinylene, quinazolinyl, quinazolinylene, quinolinyl, quinolinylene, isoquinolyl, isoquinolylene, indolyl, and indolylene.

Unless specified otherwise, aliphatic, heteroaliphatic, oxyaliphatic, alkyl, alkylene, alkenyl, alkynyl, cycloalkyl, heterocycloalkyl, aryl, and heteroaryl mentioned herein include both substituted and unsubstituted moieties. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_2$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on aliphatic, heteroaliphatic, oxyaliphatic, alkyl, alkylene, alkenyl, and alkynyl include all of the above-recited substituents except $C_1$-$C_{10}$ alkyl. Cycloalkyl, heterocycloalkyl, aryl, and heteroaryl can also be fused with each other.

The biocompatible polymers described above include the polymers themselves, as well as their salts and solvates, if applicable. A salt, for example, can be formed between an anion and a positively charged group (e.g., amino) on a polymer. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a polymer. Suitable cations include sodium ion, potassium ion, magnesium ion, calcium ion, and an ammonium cation such as tetramethylammonium ion. The polymers also include those salts containing quaternary nitrogen atoms. A solvate refers to a complex formed between a polymer and a pharmaceutically acceptable solvent. Examples of a pharmaceutically acceptable solvent include water, ethanol, isopropanol, ethyl acetate, acetic acid, and ethanolamine.

Scheme (I) below shows a process of preparing an exemplary silane-containing biocompatible polymer.

Scheme (I)

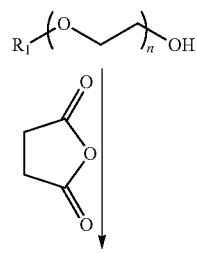

-continued

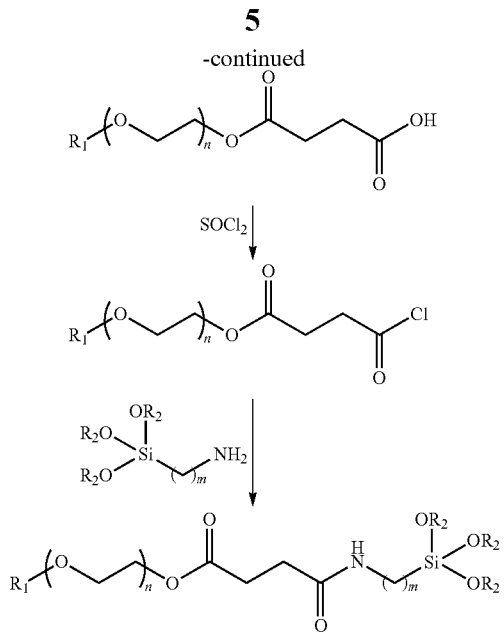

As shown in Scheme (I), alkoxyl-polyethylene glycol (molecular weight, 2000) reacts with succinic anhydride in the presence of a base (e.g., dimethylaminopyridine) to form mPEG-COOH, which is subsequently converted to mPEG-COCl using thionyl chloride. Mixing mPEG-COCl with (3-aminopropyl)-triethoxysilane yields mPEG-silane.

A skilled person in the art can modify the process shown in Scheme (I) above to prepare biocompatible polymers using well-known methods. See R. Larock, Comprehensive Organic Transformations (VCH Publishers 1989); T. W. Greene and P. G. M. Wuts, Protective Groups in Organic Synthesis ($3^{rd}$ Ed., John Wiley and Sons 1999); L. Fieser and M. Fieser, Fieser and Fieser's Reagents for Organic Synthesis (John Wiley and Sons 1994); and L. Paquette, ed., Encyclopedia of Reagents for Organic Synthesis (John Wiley and Sons 1995) and subsequent editions thereof. Specific routes that can be used to synthesize the biocompatible polymers can be found in: (a) Rist et al., Molecules 2005, 10, 1169-1178, (b) Koheler et al., JACS, 2004, 126, 7206-7211; and (c) Zhang et al., Biom mircod 2004, 6:1 33-40.

The biocompatible polymers described above each can be coated onto an iron oxide core via covalent bonding to form a biocompatible iron oxide nanoparticle. The iron oxide core has a particle size of 2 to 50 nm (e.g., 5 to 30 nm and 10 to 25 nm). Preparation of an iron oxide core is well known in the art. See Laurent et al., Chem. Rev., 2008, 108, 2064-2110.

Described below is a typical procedure to prepare an iron oxide nanoparticle. First, a biocompatible polymer is suspended in a toluene solution containing a compatible iron oxide core, followed by stirring it at room temperature for 24 hours. The resultant biocompatible magnetic nanoparticles are hydrophilic and can be extracted into a water phase and subsequently purified by ultrafiltration.

Not to be bounded by any theory, the biocompatible iron oxide nanoparticle, once administered to a patient with a condition related to iron deficiency, shows higher efficiency and lower hypersensitivity than current available parenteral iron therapies.

The specific examples below are to be construed as merely illustrative, and not limitative of the remainder of the disclosure in any way whatsoever. Without further elaboration, it is believed that one skilled in the art can, based on the description herein, utilize the present embodiments to their fullest extent. All publications cited herein are incorporated by reference in their entirety.

Preparation of Biocompatible Iron Oxide Nanoparticles

Two biocompatible iron oxide nanoparticles of these embodiments were prepared following the procedure described below.

Preparation of an Iron Oxide Core

A mixture of $FeCl_2.4H_2O$ (11.6 g; 0.058 mole), $FeCl_3.6H_2O$ (11.6 g; 0.096 mole), and water (400 mL) was stirred at 300 rpm in a three-necked flask at 25° C. A sodium hydroxide solution (2.5 N; 170 mL) was added to the flask at a rate of 47 µl/sec, resulting a pH value of 11-12. Subsequently, oleic acid (20 mL) was added and stirred for 30 minutes, followed by addition of a 6 N HCl solution to adjust the pH value to about 1. The iron oxide core thus precipitated out of the mixture was collected by filtration, and washed with water for 4-5 times to remove excess oleic acid. The iron oxide core thus obtained was then dried under vacuum to be used for coupling, as described below, with a biocompatible polymer.

Preparation of Biocompatible Polymer mPEG-Silane-750 and mPEG-Silane-2000

The biocompatible polymer mPEG-silane-750 was prepared following the procedure described below.

A mixture of 300 g (0.4 moles) of methoxy-PEG (mPEG, molecular weight 750), succinic anhydride (48 g; 0.48 moles) and 4-dimethylamino-pyridine (DMAP; 19.5 g; 0.159 moles) were allowed to sit in a 1000-mL round bottom flask under vacuum (20 Torrs) for 2 hours. 600 mL of toluene was added to the mixture, which was then stirred at 30° C. for one day to form mPEG-COOH.

Subsequently, 36 mL (0.48 moles) of thionyl chloride was added at a rate of 1 mL/min and the mixture was stirred for 2-3 hours. Thereafter, 333.8 mL (2.4 moles) of triethylamine was added at a rate of 1 mL/min to obtain pH around 6-7. After cooling to room temperature, the mixture containing mPEG-COCl was reacted with 94.5 mL (0.4 moles) of 3-aminopropyl triethoxysilane at room temperature for at least 8 hours to yield mPEG-silane-750.

mPEG-silane-750 was precipitated after 9 L of isopropyl ether was added to the reaction mixture. The solid product was collected by filtration, re-dissolved in 500 mL of toluene, and centrifuged at 5000 rpm for 5 minutes to collect a supernatant, to which was added 9 L of isopropyl ether. Brown oily liquid was separated from the isopropyl ether and dried under vacuum to obtain the biocompatible polymer mPEG-silane-750.

The biocompatible polymer mPEG-silane-2000 was prepared following the same procedure described above using a mixture of 800 g (0.4 moles) of methoxy-PEG (mPEG, molecular weight 2000), succinic anhydride (48 g; 0.48 moles) and 4-dimethylamino-pyridine (DMAP; 19.5 g; 0.159 moles).

Coupling Each of mPEG-Silane-750 and mPEG-Silane-2000 with Iron Oxide Core

Each of biocompatible polymer mPEG-silane-750 and mPEG-silane-2000 (250 g) thus obtained was suspended in 1-1.2 L of a toluene solution containing 10 g of the iron oxide core prepared as described above. The suspension was stirred for 24 hours, followed by addition of water (1.5 L) for extraction. The extracted aqueous solution was filtered with an ultra-filtration device, washed with water, and then concentrated to 100 mL to obtain a biocompatible iron oxide nanoparticle suspension. The iron oxide nanoparticle, regardless of whether it was prepared from mPEG-silane-750 or mPEG-silane-2000, is designated as iTrast.

In addition, it was found that iTrast can be administered orally to rats to achieve efficacy in treating IDA. More specifically, as shown in the table below, when iTrast (12 mg/kg) was administered orally to IDA rats, the Hb levels were unexpectedly increased from 6.1±0.5 to 11.5±0.6 at day 10.

| Group | Day after iron given, if any | Mock | 12 mg/kg iron polysaccharide | 12 mg/kg iTrast | 12 mg/kg iTrast-oral |
|---|---|---|---|---|---|
| Hb g/dL | Day 0 | 16 | 6 ± 1 | 6 ± 0.5 | 6.1 ± 0.5 |
| | Day 3 | 17.3 ± 1 | 9.9 ± 0.8 | 11.56 ± 1.2 | 9.7 ± 0.4 |
| | Day 10 | 17.1 ± 1.0 | 12.06 ± 1.0 | 13.38 ± 1.7 | 11.5 ± 0.6 |
| | Day 17 | 16.1 ± 0.7 | 12.8 ± 1.4 | 13.7 ± 1.5 | 9.1 ± 1.2 |
| | Day 23 | 16.1 ± 0.4 | 12.1 ± 1.1 | 14.6 ± 1.9 | 8.7 ± 1.2 |

Characterization of Biocompatible Iron Oxide Nanoparticle (iTrast)

Transmission electron microscopy (TEM) images of the biocompatible magnetic nanoparticle iTrast thus obtained were taken using a JEOL JEM-2100F FieldEmission Transmission Electron Microscopy. The images showed that iTrast had an iron oxide core of the dimension 10-12 nm.
Comparative Studies Between iTrast and Iron Polysaccharide in Treating Iron Deficiency Anemia (IDA)

The efficacy and safety of iTrast and iron polysaccharide in treating IDA were compared following the procedures described below.
Efficacy in Treating IDA Rats Iron deficiency was produced by feeding thirty weanling Sprague-Dawley rats (50-70 g each, Zivic-Miller, Allison Park, Pa.) an iron-deficient diet (Low Iron Diet, ICN Nutritional Biochemicals, Cleveland, Ohio). Eight control rats (mock group) received a standard diet (Purina Rat Chow, Ralston Purina, St. Louis, Mo.). All rats were housed in polyethylene cages with stainless steel tops. In about three weeks, hemoglobin (Hb) levels of the thirty IDA rats dropped from about 16 g/dL to about 6 g/dL. The Hb levels were determined following the procedures described in *Nutrition and Metabolic Insights* 2014:7 1-6.

The comparative studies started at Day 0 when the Hb levels of the mock group rats were about 16 g/dL and those of the thirty IDA rats were about 6 g/dL. See the table below. The IDA rats were intravenously (IV) injected with iron polysaccharide (FERAHEME, AMAG Pharmaceuticals, Waltham, Mass., US; 12 mg/kg) or iTrast particles (12 mg/kg). At days 0, 3, 10, 17, and 23, blood from each rat of the three groups, i.e., the mock group, the iron polysaccharide-treated group, and the iTrast-treated group, was collected, serum was prepared therefrom, and the Hb levels were determined.

Referring back to the table below, at Day 3, the Hb levels of the iTrast-treated IDA rats were unexpectedly boosted about 93% (from about 6 g/dL to about 11.56 g/dL), while the Hb levels of the iron polysaccharide-treated IDA rats only increased about 65% (from about 6 g/dL to about 9.9 g/dL). At Day 23, the Hb levels of the iTrast-treated IDA rats unexpectedly increased about 250% (from about 6 g/dL to about 14.6 g/dL), close to those of the mock rats (about 16.1 g/dL), while the Hb levels of the iron polysaccharide-treated IDA rats were significantly lower (about 12.1 g/dL). The data indicate that iTrast is more effective than iron polysaccharide in treating IDA. Further, it was found that the Hb levels of IDA rats treated with iTrast at 4 mg/kg were unexpectedly increased to the comparable levels as that of IDA rats treated with iron polysaccharide at 12 mg/kg.

Safety Indicated by Swollen Thickness of Mouse Paws

BALB/c mice (The National Laboratory Animal Center, Taipei) were sensitized with Ovalbumin (OVA) and Incomplete Freund's Adjuvant (IFA). At day 7, these mice were challenged with 0.1 mg/kg OVA, 12 mg/kg iron polysaccharide, or 12 mg/kg iTrast. The swollen thickness of paws at 24 hrs after the challenge was measured. The OVA challenged mice, the iron polysaccharide challenged mice, and the iTrast challenged mice had swollen thicknesses of paws of 0.42 mm, 0.20 mm, and 0.08 mm, respectively. The results demonstrated that (1) the OVA challenged mice had more severe swollen paws than the other mice, and (2) the iron polysaccharide challenges induced a much greater swollen thickness of paws than the iTrast challenges, indicating iTrast is unexpectedly safer than iron polysaccharide.
Safety Indicated by Oxidative Stress Response in Rats IDA rats (The National Laboratory Animal Center, Taipei) were IV injected with 12 mg/kg iTrast or iron polysaccharide. At Day 23, the rats were sacrificed, their spleens collected, and the splenocytes isolated for examination of oxidative stress response. A commercial kit, i.e., Total ROS/Superoxide detection kit (ENZ-51010; Enzo Life Sciences, Inc., NY), was used to measure real-time global levels of reactive oxygen species and superoxide in living cells.

The results show that iron polysaccharide caused more oxidative stress than iTrast. Namely, the number of positive cells in the iTrast-treated group was twice that in the iron polysaccharide-treated group, further indicating iTrast is unexpectedly safer than iron polysaccharide. Note that the positive cells are defined as cells having a florescence intensity value of $10^2$-$10^3$ over background by flow cytometry analysis.
Safety Indicated by Free Iron Level in Rats IDA rats (The National Laboratory Animal Center, Taipei) were IV injected with 12 mg/kg iTrast or iron polysaccharide. At Day 23, blood from each rat of the two groups, i.e., the iron polysaccharide-treated group and the iTrast-treated group, was collected, serum was prepared therefrom, and the free iron levels were determined following the procedures described in *Expert Rev Hematol.* 2012; 5:229-241 and *Nutrition and Metabolic Insights* 2014:7 1-6.

Referring to the table below, at day 23, the free iron levels of the iron polysaccharide-treated rats were about doubled (from about 60 ng/dL to about 128 ng/dL), while the free iron levels of the iTrast-treated rats were only slightly increased (from about 63 ng/dL to about 67 ng/dL). The results indicate that iTrast is unexpectedly safer than iron polysaccharide.

| | Day after iron given | 12 mg/kg iron polysaccharide | 12 mg/kg iTrast |
|---|---|---|---|
| Iron ng/dL | Day 0 | 60 ± 4 | 63 ± 5.8 |
| | Day 3 | 124.2 ± 25.6 | 77 ± 11.5 |
| | Day 10 | 106 ± 23.0 | 82.6 ± 19.4 |
| | Day 17 | 112.8 ± 23.4 | 84.2 ± 21.4 |
| | Day 23 | 128 ± 13 | 67 ± 21 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims. It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method of treating iron deficiency anemia in a patient, comprising:
   identifying a patient having iron deficiency anemia; and administering an effective amount of biocompatible iron oxide nanoparticles to the patient, the biocompatible iron oxide nanoparticles each containing an iron oxide core that is covered by one or more biocompatible polymers, each of which has a polyethylene glycol group, a silane group, and a linker linking, via a covalent bond, the polyethylene glycol group and the silane group.

2. The method of claim 1, wherein the iron oxide core has a size of 2 to 50 nm; the polyethylene glycol group has 5-1000 oxyethylene units; the silane group further comprises a $C_{1-10}$ alkylene group; and the linker is O, S, Si, $C_1$-$C_6$ alkylene, a carbonyl moiety containing two carbonyl groups and 2-20 carbon atoms, or a group having one of the following formula:

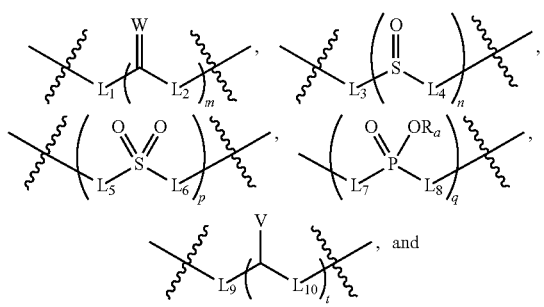

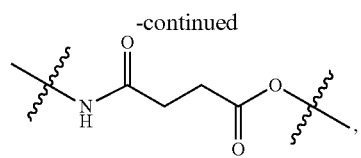

in which each of m, n, p, q, and t, independently, is 1-6; W is O, S, or $NR_b$; each or $L_1$, $L_3$, $L_5$, $L_7$, and $L_9$, independently, is a bond, O, S, or $NR_c$; each of $L_2$, $L_4$, $L_6$, $L_8$, and $L_{10}$, independently, is a bond, O, S, or $NR_d$; and V is $OR_e$, $SR_f$, or $NR_gR_h$, each of $R_a$, $R_b$, $R_c$, $R_d$, $R_e$, $R_f$, $R_g$, and $R_h$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical.

3. The method of claim 2, wherein the biocompatible iron oxide nanoparticles each have a particle size of 3-1000 nm.

4. The method of claim 3, wherein the biocompatible iron oxide nanoparticles each have a particle size of 15-200 nm.

5. The method of claim 1, wherein the iron oxide core has a size of 2 to 50 nm; the polyethylene glycol group has 10 to 200 oxyethylene units; the silane group further comprises $C_3$-$C_{10}$ alkylene; and the linker is a carbonyl moiety of the following formula:

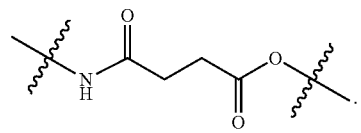 [SMILES: *NC(=O)CCC(=O)O*]

6. The method of claim 5, wherein the biocompatible iron oxide nanoparticles each have a particle size of 3-1000 nm.

7. The method of claim 6, wherein the biocompatible iron oxide nanoparticles each have a particle size of 15-200 nm.

8. The method of claim 1, wherein the biocompatible iron oxide nanoparticles each have a particle size of 3-1000 nm.

9. The method of claim 8, wherein the biocompatible iron oxide nanoparticles each have a particle size of 15-200 nm.

10. The method of claim 1, wherein the iron oxide core is covered by one or more biocompatible polymers having the following formula:

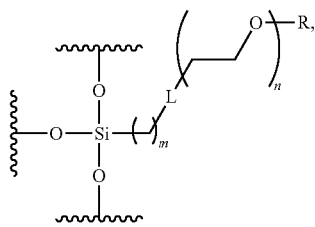

in which
R is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, heteroaryl, a $C_1$-$C_{10}$ carbonyl group, or a $C_1$-$C_{10}$ amine group;
L is a linker;
m is 1 to 10; and
n is 5 to 1000.

11. The method of claim 10, wherein the linker is O, S, Si, $C_1$-$C_6$ alkylene, a carbonyl moiety containing two carbonyl groups and 2-20 carbon atoms, or a group having one of the following formula:

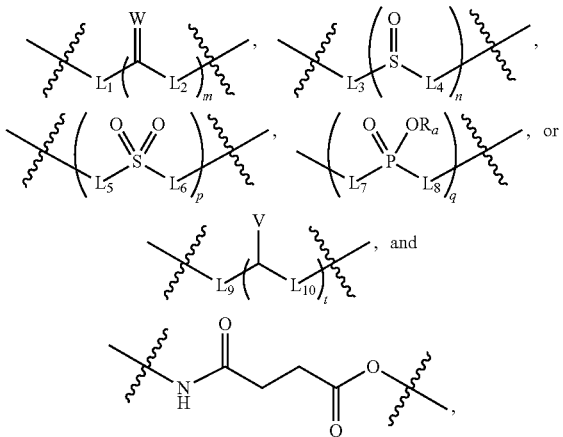

in which each of m, n, p, q, and t, independently, is 1-6; W is O, S, or $NR_b$; each of $L_1$, $L_3$, $L_5$, $L_7$, and $L_9$, independently, is a bond, O, S, or $NR_c$; each of $L_2$, $L_4$, $L_6$, $L_8$, and $L_{10}$, independently, is a bond, O, S, or $NR_d$; and V is $OR_e$, $SR_f$, or $NR_gR_h$, each of $R_a$, $R_b$, $R_c$, $R_d$, $R_e$, $R_f$, $R_g$, and $R_h$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical.

12. The method of claim 1, wherein the iron oxide core is covered by one or more biocompatible polymers having the following formula:

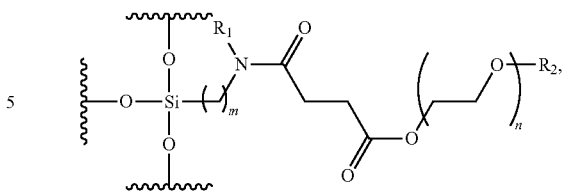

in which $R_1$ is H, $C_1$-$C_6$ alkyl, $C_2$-$C_6$ alkenyl, $C_2$-$C_6$ alkynyl, $C_3$-$C_{10}$ cycloalkyl, $C_1$-$C_{10}$ heterocycloalkyl, aryl, heteroaryl, a $C_1$-$C_{10}$ carbonyl group, or a $C_1$-$C_{10}$ amine group;

$R_2$ is H, $C_1$-$C_6$ alkyl, $C_2$-$C_6$ alkenyl, $C_2$-$C_6$ alkynyl, $C_3$-$C_{10}$ cycloalkyl, heterocycloalkyl, aryl, or heteroaryl;

m is 1 to 10; and n is 5 to 1000.

13. The method of claim 12, wherein the biocompatible iron oxide nanoparticles each have a particle size of 3-1000 nm.

14. The method of claim 13, wherein the biocompatible iron oxide nanoparticles each have a particle size of 15-200 nm.

15. The method of claim 12, wherein $R_1$ is H; $R_2$ is H, $C_1$-$C_6$ alkyl, a $C_1$-$C_{10}$ carbonyl group, or a $C_1$-$C_{10}$ amine group; m is 3 to 10; and n is 10 to 200.

16. The method of claim 15, wherein the biocompatible iron oxide nanoparticles each have a particle size of 3-1000 nm.

17. The method of claim 16, wherein the biocompatible iron oxide nanoparticles each have a particle size of 15-200 nm.

18. The method of claim 1, wherein the effective amount of biocompatible iron oxide nanoparticles is 12 mg per kg of body weight.

* * * * *